United States Patent
Yu et al.

(10) Patent No.: US 8,792,980 B2
(45) Date of Patent: *Jul. 29, 2014

(54) CARDIAC RESYNCHRONIZATION SYSTEM EMPLOYING MECHANICAL MEASUREMENT OF CARDIAC WALLS

(75) Inventors: Yinghong Yu, Shoreview, MN (US); Jiang Ding, Shoreview, MN (US); Qingsheng Zhu, Wexford, PA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 807 days.

This patent is subject to a terminal disclaimer.

(21) Appl. No.: 12/980,417

(22) Filed: Dec. 29, 2010

(65) Prior Publication Data
US 2011/0093031 A1    Apr. 21, 2011

Related U.S. Application Data

(63) Continuation of application No. 11/549,676, filed on Oct. 16, 2006, now Pat. No. 7,904,155, which is a continuation of application No. 10/005,092, filed on Dec. 5, 2001, now Pat. No. 7,127,289.

(51) Int. Cl.
*A61N 1/368* (2006.01)
*A61N 1/365* (2006.01)

(52) U.S. Cl.
CPC .................................. *A61N 1/36578* (2013.01)
USPC .............................................. 607/9; 607/18

(58) Field of Classification Search
CPC ................................................ A61N 1/36578
See application file for complete search history.

(56) References Cited

U.S. PATENT DOCUMENTS

| | | | |
|---|---|---|---|
| 4,928,688 | A | 5/1990 | Mower |
| 4,936,304 | A | 6/1990 | Kresh et al. |
| 4,993,427 | A | 2/1991 | Barr et al. |
| 5,271,392 | A | 12/1993 | Ferek-Petric |
| 5,304,208 | A | 4/1994 | Inguaggiato et al. |
| 5,496,361 | A | 3/1996 | Moberg et al. |
| 5,501,702 | A | 3/1996 | Plicchi et al. |
| 5,626,623 | A | 5/1997 | Kieval et al. |
| 5,628,777 | A | 5/1997 | Moberg et al. |
| 5,788,643 | A | 8/1998 | Feldman |
| 5,836,987 | A | 11/1998 | Baumann et al. |

(Continued)

OTHER PUBLICATIONS

"Pacing and Clinical Electrophysiology", vol. 24, No. 4, Part II, (Apr. 2001), p. 732.

(Continued)

*Primary Examiner* — Kennedy Schaetzle
(74) *Attorney, Agent, or Firm* — Schwegman, Lundberg & Woessner, P.A.

(57) ABSTRACT

Methods and devices are disclosed for employing mechanical measurements to synchronize contractions of ventricular wall locations. Accelerometers that may be placed within electrode leads are positioned at ventricular wall locations, such as the left ventricle free wall, right ventricle free wall, and the anterior wall/septum wall. The accelerometers produce signals in response to the motion of the ventricular wall locations. A processor may then compare the signals to determine a difference in the synchronization of the ventricular wall location contractions. The difference in synchronization can be determined in various ways such as computing a phase difference and/or amplitude difference between the accelerometer signals. One or more stimulation pulses may be provided per cardiac cycle to resynchronize the contractions as measured by the accelerometers to thereby constantly and automatically optimize the cardiac resynchronization therapy.

20 Claims, 5 Drawing Sheets

(56) References Cited

U.S. PATENT DOCUMENTS

| | | | |
|---|---|---|---|
| 6,002,963 | A | 12/1999 | Mouchawar et al. |
| 6,070,100 | A | 5/2000 | Bakels et al. |
| 6,076,015 | A | 6/2000 | Hartley et al. |
| 6,077,236 | A | 6/2000 | Cunningham |
| 6,122,545 | A | 9/2000 | Struble et al. |
| 6,219,579 | B1 | 4/2001 | Bakels et al. |
| 6,223,079 | B1 | 4/2001 | Bakels et al. |
| 6,223,082 | B1 | 4/2001 | Bakels et al. |
| 6,238,420 | B1 | 5/2001 | Bakels et al. |
| 6,278,894 | B1 | 8/2001 | Salo et al. |
| 6,280,389 | B1 | 8/2001 | Ding et al. |
| 6,308,095 | B1 | 10/2001 | Hsu et al. |
| 6,422,990 | B1 | 7/2002 | Prem |
| 6,442,424 | B1 | 8/2002 | Ben-Haim et al. |
| 6,449,503 | B1 | 9/2002 | Hsu |
| 6,540,699 | B1 * | 4/2003 | Smith ............................ 600/587 |
| 6,556,866 | B2 | 4/2003 | Dal Molin et al. |
| 6,751,503 | B1 | 6/2004 | Kroll |
| 6,751,504 | B2 | 6/2004 | Fishler |
| 6,754,530 | B2 | 6/2004 | Bakels et al. |
| 6,885,889 | B2 | 4/2005 | Chinchoy |
| 6,923,772 | B2 | 8/2005 | Yu |
| 7,010,347 | B2 | 3/2006 | Schecter |
| 7,127,289 | B2 | 10/2006 | Yu et al. |
| 7,206,634 | B2 | 4/2007 | Ding et al. |
| 7,283,873 | B1 | 10/2007 | Park et al. |
| 7,440,803 | B2 | 10/2008 | Ni et al. |
| 7,904,155 | B2 * | 3/2011 | Yu et al. ............................ 607/9 |
| 8,126,548 | B2 | 2/2012 | Ding |
| 8,295,927 | B2 | 10/2012 | Ding et al. |
| 8,417,334 | B2 * | 4/2013 | Hill et al. ............................ 607/9 |
| 2001/0010009 | A1 | 7/2001 | Bakels et al. |
| 2001/0012953 | A1 | 8/2001 | Molin et al. |
| 2002/0002389 | A1 | 1/2002 | Bradley et al. |
| 2003/0100925 | A1 | 5/2003 | Pape et al. |
| 2003/0105496 | A1 | 6/2003 | Yu et al. |
| 2003/0216657 | A1 | 11/2003 | Holmstrom et al. |
| 2004/0015081 | A1 | 1/2004 | Kramer et al. |
| 2004/0015196 | A1 | 1/2004 | Holstrom et al. |
| 2004/0019365 | A1 | 1/2004 | Ding et al. |
| 2004/0049112 | A1 | 3/2004 | Yu et al. |
| 2004/0049238 | A1 | 3/2004 | Jarverud |
| 2004/0078058 | A1 | 4/2004 | Holmstrom et al. |
| 2005/0038481 | A1 | 2/2005 | Chinchoy et al. |
| 2005/0043895 | A1 | 2/2005 | Schechter |
| 2005/0102002 | A1 | 5/2005 | Salo et al. |
| 2006/0271119 | A1 | 11/2006 | Ni et al. |
| 2006/0271121 | A1 | 11/2006 | Ding et al. |
| 2007/0066905 | A1 | 3/2007 | Zhang |
| 2007/0129781 | A1 | 6/2007 | Yu et al. |
| 2008/0114410 | A1 | 5/2008 | Ding et al. |
| 2009/0048637 | A1 | 2/2009 | Ni et al. |

OTHER PUBLICATIONS

"U.S. Appl. No. 10/005,092, Advisory Action mailed Apr. 22, 2005", 2 pgs.

"U.S. Appl. No. 10/005,092, Final Office Action mailed Jan. 31, 2005", 5 pgs.

"U.S. Appl. No. 10/005,092, Final Office Action mailed Jun. 29, 2005", 7 pgs.

"U.S. Appl. No. 10/005,092, Non Final Office Action mailed May 19, 2004", 8 pgs.

"U.S. Appl. No. 10/005,092, Notice of Allowance mailed Jun. 13, 2006", 4 pgs.

"U.S. Appl. No. 10/005,092, Notice of Allowance mailed Sep. 19, 2005", 4 pgs.

"U.S. Appl. No. 10/005,092, Response filed Mar. 31, 2005 to Final Office Action mailed Jan. 31, 2005", 16 pgs.

"U.S. Appl. No. 10/005,092, Response filed Aug. 25, 2005 to Final Office Action mailed Jun. 29, 2005", 12 pgs.

"U.S. Appl. No. 10/005,092, Response filed Nov. 19, 2004 to Non Final Office Action mailed May 19, 2004", 17 pgs.

"U.S. Appl. No. 10/005,092, Supplemental Notice of Allowability mailed Jul. 12, 2006", 3 pgs.

"U.S. Appl. No. 11/110,418, Non-Final Office Action mailed Apr. 14, 2009", 13 pgs.

"U.S. Appl. No. 11/110,418, Non-Final Office Action mailed Oct. 30, 2008", 14 pgs.

"U.S. Appl. No. 11/110,418, Notice of Allowance mailed Jul. 28, 2009", 7 pgs.

"U.S. Appl. No. 11/110,418, Response filed Jan. 30, 2009 to Non Final Office Action mailed Oct. 30, 2008", 15 pgs.

"U.S. Appl. No. 11/110,418, Response filed May 11, 2009 to Non Final Office Action mailed Apr. 14, 2009", 12 pgs.

"U.S. Appl. No. 11/136,894, Final Office Action mailed Oct. 18, 2007", 9 pgs.

"U.S. Appl. No. 11/136,894, Non Final Office Action mailed Apr. 26, 2007", 8 pgs.

"U.S. Appl. No. 11/136,894, Response filed Jul. 26, 2007 to Non Final Office Action mailed Apr. 26, 2007", 15 pgs.

"U.S. Appl. No. 11/208,922, Advisory Action mailed Mar. 11, 2009", 3 pgs.

"U.S. Appl. No. 11/208,922, Appeal Brief filed Aug. 3, 2009", 30 pgs.

"U.S. Appl. No. 11/208,922, Decision on Pre-Appeal Brief mailed Jun. 3, 2009", 2 pgs.

"U.S. Appl. No. 11/208,922, Final Office Action mailed Dec. 23, 2008", 8 pgs.

"U.S. Appl. No. 11/208,922, Interview Summary mailed Jun. 19, 2008", 2 pgs.

"U.S. Appl. No. 11/208,922, Non Final Office Action mailed Apr. 4, 2008", 14 pgs.

"U.S. Appl. No. 11/208,922, Pre-Appeal Brief Request for Review filed Mar. 23, 2009", 5 pgs.

"U.S. Appl. No. 11/208,922, Response filed Feb. 11, 2008 to Restriction Requirement mailed Jan. 10, 2008", 11 pgs.

"U.S. Appl. No. 11/208,922, Response filed Feb. 23, 2009 to Final Office Action mailed Dec. 23, 2008", 14 pgs.

"U.S. Appl. No. 11/208,922, Response filed Jun. 30, 2008 to Non Final Office Action mailed Apr. 4, 2008", 15 pgs.

"U.S. Appl. No. 11/208,922, Restriction Requirement mailed Jan. 10, 2008", 8 pgs.

"U.S. Appl. No. 11/232,057, Appeal Brief filed Sep. 17, 2009", 29 pgs.

"U.S. Appl. No. 11/232,057, Final Office Action mailed Apr. 20, 2009", 9 pgs.

"U.S. Appl. No. 11/232,057, Non Final Office Action mailed Sep. 22, 2008", 6 pgs.

"U.S. Appl. No. 11/232,057, Response filed Jan. 20, 2009 to Non Final Office Action mailed Sep. 22, 2008", 15 pgs.

"U.S. Appl. No. 11/232,057, Response filed Jul. 10, 2007 to Non Final Office Action mailed Apr. 10, 2007", 16 pgs.

"U.S. Appl. No. 11/232,057, Response filed Jun. 22, 2009 to Final Office Action mailed Apr. 20, 2009", 15 pgs.

"U.S. Appl. No. 11/232,057, Restriction Requirement mailed Jul. 25, 2008", 7 pgs.

"U.S. Appl. No. 11/264,941, Advisory Action mailed Dec. 21, 2007", 3 pgs.

"U.S. Appl. No. 11/264,941, Final Office Action mailed Sep. 24, 2007", 8 pgs.

"U.S. Appl. No. 11/264,941, Interview Summary filed Mar. 20, 2008", 1 pg.

"U.S. Appl. No. 11/264,941, Non Final Office Action mailed Apr. 10, 2007", 8 pgs.

"U.S. Appl. No. 11/264,941, Notice of Allowance mailed Feb. 20, 2008", 12 pgs.

"U.S. Appl. No. 11/264,941, Notice of Allowance mailed Jun. 16, 2008", 9 pgs.

"U.S. Appl. No. 11/264,941, Response filed Jan. 24, 2008 to Final Office Action mailed Sep. 24, 2007", 15 pgs.

"U.S. Appl. No. 11/264,941, Response filed Feb. 22, 2007 to Restriction Requirement dated Jan. 22, 2007", 14 pgs.

"U.S. Appl. No. 11/264,941, Response filed Jul. 10, 2007 to Non Final Office Action mailed Apr. 10, 2007", 16 pgs.

"U.S. Appl. No. 11/264,941, Response filed Nov. 26, 2007 to Final Office Action mailed Sep. 24, 2007", 16 pgs.

(56) References Cited

OTHER PUBLICATIONS

"U.S. Appl. No. 11/264,941, Restriction Requirement mailed Jan. 22, 2007", 5 pgs.

"U.S. Appl. No. 11/264,941, Summary of Interview dated Feb. 28, 2008", 2 pgs.

"U.S. Appl. No. 11/549,676, Examiner Interview Summary mailed Jun. 15, 2009", 4 pgs.

"U.S. Appl. No. 11/549,676, Non Final Office Action mailed Apr. 6, 2009", 7 pgs.

"U.S. Appl. No. 11/549,676, Non-Final Office Action mailed Oct. 9, 2009", 6 pgs.

"U.S. Appl. No. 11/549,676, Notice of Allowance mailed Apr. 19, 2010", 4 pgs.

"U.S. Appl. No. 11/549,676, Notice of Allowance mailed Oct. 21, 2010", 6 pgs.

"U.S. Appl. No. 11/549,676, Response filed Jan. 13, 2010 to Non Final Office Action mailed Oct. 9, 2009", 9 pgs.

"U.S. Appl. No. 11/549,676, Response filed Jun. 26, 2009 to Non Final Office Action mailed Apr. 6, 2009", 11 pgs.

"U.S. Appl. No. 11/549,676, Supplemental Amendment filed Aug. 9, 2010", 7 pgs.

Abe, H., et al., "Asynchronous Relaxation of the Ischemic Left Ventricle", Japanese Circulation Journal, 46(1), (1982), 103-112.

Yu, C.-M., et al., "High Prevalence of Left Ventricular Systolic and Diastolic Asynchrony in Patients With Congestive Heart Failure and Normal QRS Duration", Heart, vol. 89, (2003), 54-60.

Yu, Yinghong, et al., "A Cardiac Resynchronization System Employing Mechanical Measurement of Cardiac Walls", U.S. Appl. No. 11/549,676, filed Oct. 16, 2006, 28 pgs.

Yu, Yinghong, et al., "Biventricular mechanical asynchrony predicts hemodynamic effects of uni- and biventricular pacing", Am J Physiol Heart Circ Physiol, vol. 285, (2003), H2788-H2796.

Zhang, Y., "Intracardiac Impedance and Its Applications", U.S. Appl. No. 11/208,922, filed Aug. 22, 2005, 36 Pgs.

"U.S. Appl. No. 11/136,894, Examiner Interview Summary mailed Apr. 22, 2008", 1 pg.

"U.S. Appl. No. 11/136,894, Response filed Feb. 22, 2007 to Restriction Requirement mailed Jan. 22, 2007", 18 pgs.

"U.S. Appl. No. 11/136,894, Restriction Requirement mailed Jan. 22, 2007", 5 pgs.

"U.S. Appl. No. 12/016,830, Non Final Office Action mailed Jun. 8, 2011", 8 pgs.

"U.S. Appl. No. 12/016,830, Notice of Allowance mailed Oct. 19, 2011", 7 pgs.

"U.S. Appl. No. 12/016,830, Response filed Sep. 8, 2011 to Non Final Office Action mailed Jun. 8, 2011", 13 pgs.

"U.S. Appl. No. 12/254,631, Non Final Office Action mailed Nov. 14, 2011", 6 pgs.

"U.S. Appl. No. 12/254,631, Notice of Allowance mailed Mar. 2, 2012", 7 pgs.

"U.S. Appl. No. 12/254,631, Notice of Allowance mailed Jun. 18, 2012", 7 pgs.

"U.S. Appl. No. 12/254,631, Response filed Feb. 9, 2012 to Non Final Office Action mailed Nov. 14, 2011", 9 pgs.

"U.S. Appl. No. 13/405,383, Non Final Office Action mailed Apr. 11, 2013", 9 pgs.

"U.S. Appl. No. 13/405,383, Response filed Mar. 26, 2013 to Restriction Requirement mailed Feb. 27, 2013", 6 pgs.

"U.S. Appl. No. 13/405,383, Restriction Requirement mailed Feb. 27, 2013", 8 pgs.

\* cited by examiner

CARDIAC RESYNCHRONIZATION SYSTEM EMPLOYING MECHANICAL MEASUREMENT OF CARDIAC WALLS

CROSS REFERENCE TO RELATED APPLICATIONS

This application is a continuation of U.S. patent application Ser. No. 11/549,676, filed on Oct. 16, 2006, issued as U.S. Pat. No. 7,904,155, which is a continuation of U.S. patent application Ser. No. 10/005,092, filed on Dec. 5, 2001, issued as U.S. Pat. No. 7,127,289, the specifications of which are incorporated herein by reference.

TECHNICAL FIELD

The present invention is directed to cardiac resynchronization (CRT) systems. More specifically, the present invention is directed to CRT systems that employ mechanical measurements of cardiac wall motion when synchronizing ventricular contraction.

BACKGROUND

The heart is a muscular organ comprising multiple chambers that operate in concert to circulate blood throughout the body's circulatory system. As shown in FIG. 1, the heart 100 includes a right-side portion or pump 102 and a left-side portion or pump 104. The right-side portion 102 includes a right atrium 106 and a right ventricle 108. Similarly, the left-side portion 104 includes a left atrium 110 and a left ventricle 112. Oxygen-depleted blood returning to the heart 100 from the body collects in the right atrium 106. When the right atrium 106 fills, the oxygen-depleted blood passes into the right ventricle 108 where it can be pumped to the lungs (not shown) via the pulmonary arteries 117. Within the lungs, waste products (e.g., carbon dioxide) are removed from the blood and expelled from the body and oxygen is transferred to the blood. Oxygen-rich blood returning to the heart 100 from the lungs via the pulmonary veins (not shown) collects in the left atrium 110. The circuit between the right-side portion 102, the lungs, and the left atrium 110 is generally referred to as the pulmonary circulation. After the left atrium 110 fills, the oxygen-rich blood passes into the left ventricle 112 where it can be pumped throughout the entire body. In so doing, the heart 100 is able to supply oxygen to the body and facilitate the removal of waste products from the body.

To circulate blood throughout the body's circulatory system as described above, a beating heart performs a cardiac cycle that includes a systolic phase and a diastolic phase. During the systolic phase (e.g., systole), the ventricular muscle cells of the right and left ventricles 108, 112 contract to pump blood through the pulmonary circulation and throughout the body, respectively. Conversely, during the diastolic phase (e.g., diastole), the ventricular muscle cells of the right and left ventricles 108, 112 relax, during which the right and left atriums 106, 110 contract to force blood into the right and left ventricles 108, 112, respectively. Typically, the cardiac cycle occurs at a frequency between 60 and 100 cycles per minute and can vary depending on physical exertion and/or emotional stimuli, such as, pain or anger.

The contractions of the muscular walls of each chamber of the heart 100 are controlled by a complex conduction system that propagates electrical signals to the heart muscle tissue to effectuate the atrial and ventricular contractions necessary to circulate the blood. As shown in FIG. 2, the complex conduction system includes an atrial node 120 (e.g., the sinoatrial node) and a ventricular node 122 (e.g., the atrioventricular node). The sinoatrial node 120 initiates an electrical impulse that spreads through the muscle tissues of the right and left atriums 106, 110 and the atrioventricular node 122. As a result, the right and left atriums 106, 110 contract to pump blood into the right and left ventricles 108, 112 as discussed above.

At the atrioventricular node 122, the electrical signal is momentarily delayed before propagating through the right and left ventricles 108, 112. Within the right and left ventricles 108, 112, the conduction system includes right and left bundle branches 126, 128 that extend from the atrioventricular node 122 via the Bundle of His 124. The electrical impulse spreads through the muscle tissues of the right and left ventricles 108, 112 via the right and left bundle branches 126, 128, respectively. As a result, the right and left ventricles 108, 112 contract to pump blood throughout the body as discussed above.

Normally, the muscular walls of each chamber of the heart 100 contract synchronously in a precise sequence to efficiently circulate the blood as described above. In particular, both the right and left atriums 106, 110 contract (e.g., atrial contractions) and relax synchronously. Shortly after the atrial contractions, both the right and left ventricles 108, 112 contract (e.g., ventricular contractions) and relax synchronously. Several disorders or arrhythmias of the heart can prevent the heart from operating normally, such as, blockage of the conduction system, heart disease (e.g., coronary artery disease), abnormal heart valve function, or heart failure.

Blockage in the conduction system can cause a slight or severe delay in the electrical impulses propagating through the atrioventricular node 122, causing inadequate ventricular relaxation and filling. In situations where the blockage is in the ventricles (e.g., the right and left bundle branches 126, 128), the right and/or left ventricles 108, 112 can only be excited through slow muscle tissue conduction. As a result, the muscular walls of the affected ventricle (108 and/or 112) do not contract synchronously (e.g., asynchronous contraction), thereby, reducing the overall effectiveness of the heart 100 to pump oxygen-rich blood throughout the body.

Various medical procedures have been developed to address these and other heart disorders. In particular, cardiac resynchronization therapy ("CRT") can be used to improve the conduction pattern and sequence of the heart 100. CRT involves the use of an artificial electrical stimulator that is surgically implanted within the patient's body. Leads from the stimulator can be affixed at a desired location within the heart 100 to effectuate synchronous atrial and/or ventricular contractions. Typically, the location of the leads (e.g., stimulation site) is selected based upon the severity and/or location of the blockage. Electrical stimulation signals can be delivered to resynchronize the heart, thereby, improving cardiac performance.

In conventional CRT systems, establishing synchronization of ventricular walls involves measuring intrinsic electrical signals traveling through the ventricles and then applying an educated guess to time application of stimulation signals that are intended to provide the resynchronization. The educated guess employed by the CRT device is generally based upon empirical data of heart failure patients' responses to application of electrical signals with varying timing, amplitude, and/or location. However, the success of the stimulation signals in terms of the mechanical response of the ventricles can only be known with certainty by directly measuring the mechanical response occurring due to application of the stimulation signal.

Observing the mechanical response is useful when optimizing CRT because there may be no known correlation between the electrical activity and mechanical response of a particular patient's heart. Improving the heart's mechanical response is ultimately the goal of CRT, and therefore controlling the mechanical response by measuring only electrical activity is not ideal. An additional drawback to conventional CRT methods of optimization includes a requirement that the CRT stimulation be turned off so that the implanted electrodes can sense rather than stimulate. This causes the measured electrical activity used to optimize the CRT device to be even further removed from the heart's mechanical response to stimulation from CRT.

Direct mechanical measurements of ventricular wall synchronization allow the mechanical effects of manipulating the electrical activity to be observed. Direct mechanical measurements can be performed by ultrasound techniques or other similarly cumbersome and time-consuming methods that are available only when the patient is visiting a health care provider. These relatively infrequent follow-up visits are inadequate for constantly optimizing the CRT therapy because the mechanical response of the heart may change as the patient's physical condition changes over time. Thus, the patient's CRT device may become inefficient during the time between visits. Additionally, these direct mechanical measurements are performed by systems distinct from the patient's CRT device and do not automatically optimize CRT based on the mechanical response but require intervention by a physician.

Therefore, there is a need for CRT methods and devices that can constantly and/or automatically optimize CRT for a patient based on mechanical response of the patient's ventricles.

SUMMARY

Embodiments of the present invention establish synchronization of ventricular wall contraction by employing direct mechanical measurement. The direct mechanical measurement of various wall locations can be compared to determine the degree of synchronization. The direct mechanical measurement may also be used on a beat-by-beat basis to determine whether to alter the parameters of the stimulation pulse(s) to maintain synchronization of the ventricular wall contraction.

The present invention may be viewed as a method of synchronizing a contraction of ventricular wall locations. The method involves sensing motion with a first accelerometer located at a first ventricular wall location to produce a first signal and sensing motion with a second accelerometer located at a second ventricular wall location to produce a second signal. The method also involves comparing the first signal to the second signal to detect a difference in synchronization of the first ventricular wall contraction and the second ventricular wall contraction.

The present invention may also be viewed as a device for synchronizing a contraction of ventricular wall locations. The device includes a first accelerometer located at a first ventricular wall location and a second accelerometer located at a second ventricular wall location. The device also includes a processing module configured to compare a first signal produced by motion of the first accelerometer to a second signal produced by motion of the second accelerometer to detect a difference in synchronization of the first ventricular wall location contraction and the second ventricular wall location contraction.

The present invention may be viewed as another device for synchronizing a contraction of ventricular wall locations. The device includes a first motion sensing means located at a first ventricular wall location for producing a first signal in response to contraction of the first ventricular wall location. The device also includes a second motion sensing means located at a second ventricular wall location for producing a second signal in response to contraction of the second ventricular wall location. Additionally, the device includes a processing means for comparing the first signal to the second signal to detect a difference in synchronization of the first ventricular wall location contraction and the second ventricular wall location contraction.

DETAILED DESCRIPTION

Figure 1:
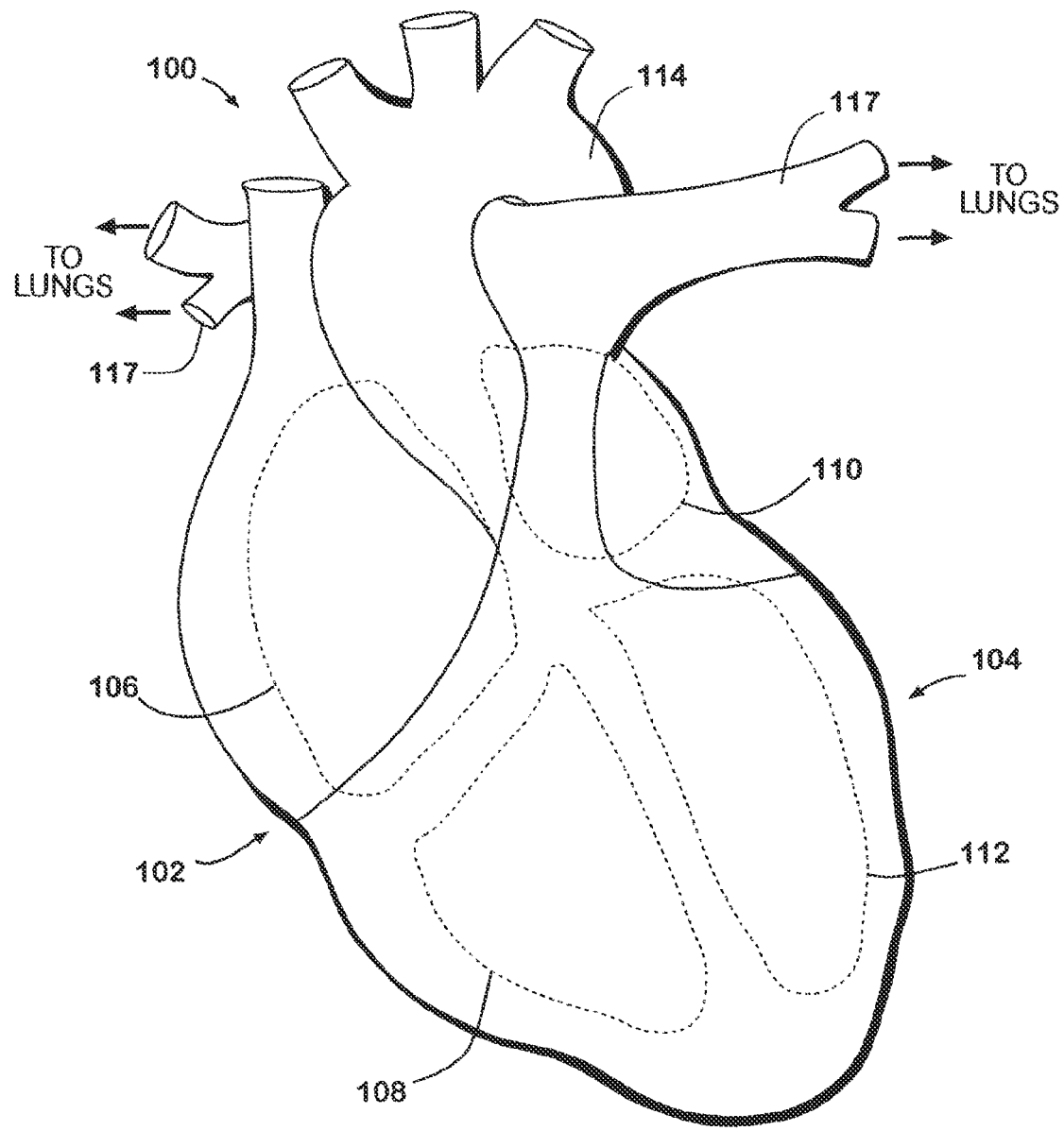
FIG. 1 is a simplified illustration depicting the primary pumping components of a human heart.
Figure 2:
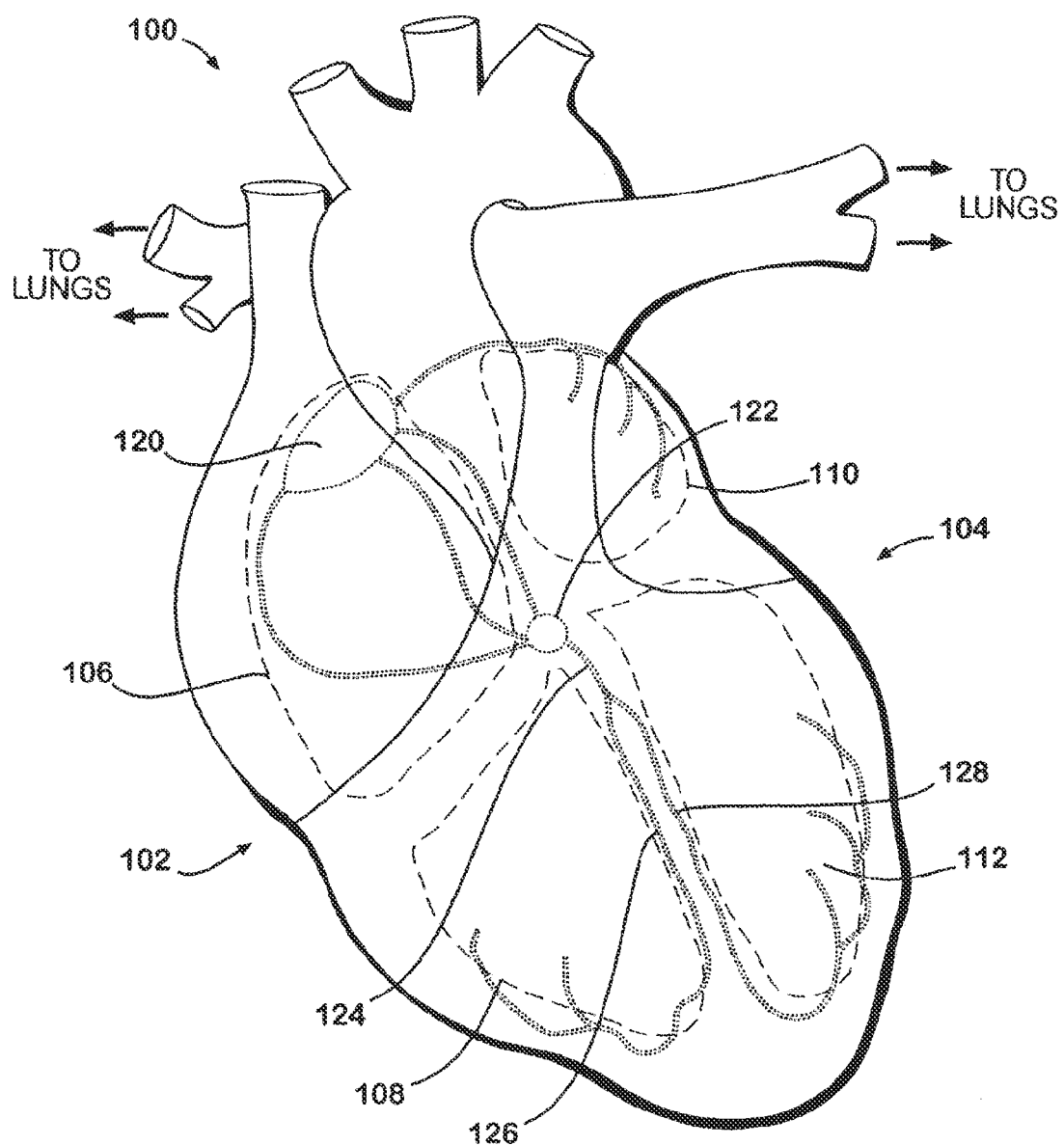
FIG. 2 is a simplified illustration depicting a human heart and the transmission paths over which a normal heart provides depolarization waves to the heart chambers.

Various embodiments of the present invention will be described in detail with reference to the drawings, wherein like reference numerals represent like parts and assemblies throughout the several views. Reference to various embodiments does not limit the scope of the present invention, which is limited only by the scope of the claims attached hereto.

Embodiments of the present invention provide CRT optimization through analysis of signals produced directly by motion of the ventricular walls. Accelerometers can be placed within electrode leads routed to the various ventricular wall locations and can enable continuous and automatic optimization of the CRT device based on the direct mechanical measurement from the accelerometer for each cardiac cycle.

Figure 3:
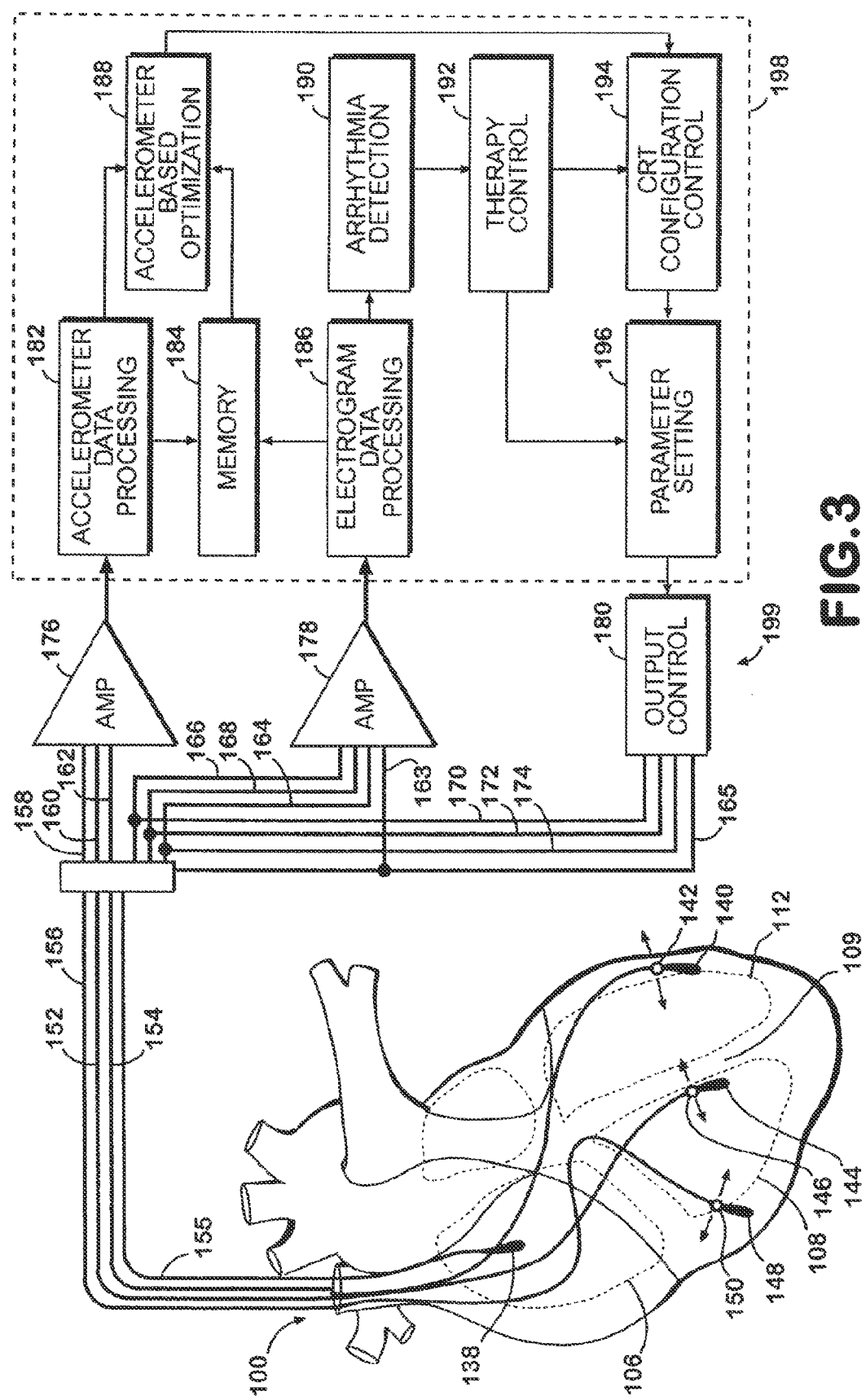
FIG. 3 is a block diagram depicting the primary components of a CRT device that is an exemplary embodiment of the present invention.

A CRT device 199 in accordance with one embodiment of the present invention is shown in FIG. 3. The CRT device 199 includes a processing module 198, which may include several sub-modules and memory 184 for implementing CRT and treating additional arrhythmia conditions such as bradycardia. Additionally, an output control module 180 is included to provide stimulation pulses to electrodes implanted on or within the heart 100 at appropriate times according to the optimized CRT. Accelerometer amplifier 176 is included to amplify the signals received from the accelerometers positioned at the various ventricular wall locations to improve the signal to noise ratio and provide a signal level and shape acceptable for processing by processing module 198. Sensing electrode amplifier 178 is included to amplify the electrical signals sensed by electrodes also positioned at the various ventricular wall locations as well as other locations including atrial positions.

The CRT device 199 is connected to an atrial electrode 138 through implantable lead 155 and to ventricular electrodes and accelerometers through implantable leads 152, 154, and 156. The atrial lead 155 passes into the right atrium 106 and is linked to the sensing amp 178 through conductor pair 163 and to an output module 180 through conductor pair 165. The atrial lead 155 is generally placed in proximity to the sin θ-atrial node 120 for proper sensing of intrinsic electrical activity and/or atrial pacing should additional arrhythmias exist within the heart 100.

The left ventricle lead 154 passes into a coronary sinus vein branch spanning the free wall location of the left ventricle 112. The left ventricle lead 154 carries an electrode conductor pair 164/174 discussed below and an accelerometer conductor pair 162. Likewise, an anterior lead 152 passes into the right ventricle 108 from the right atrium 106 through the tricuspid valve and attaches to the anterior wall comprising the septum 109 separating the right ventricle 108 and left ventricle 112. The anterior lead 152 may carry an electrode conductor pair 168/172 discussed below and an accelerometer conductor pair 160. Alternatively, the anterior lead 152 may be positioned in the anterior branch of the coronary sinus vein and extended to the septum area 109. Additionally, a right ventricle lead 156 may be included and passes through the coronary sinus vein branch that spans the free wall of the right ventricle 108. The right ventricle lead 156 may also contain an electrode conductor pair 166/170 discussed below and an accelerometer conductor pair 158.

One or more electrodes 140 may be located near a distal end of the left ventricle lead 154 and are electrically connected to the electrode conductor pair 164/174 of lead 154. One or more accelerometers 142 may also be located near the distal end of the left ventricle lead 154 and are electrically connected to the accelerometer conductor pair 162 of lead 154. The one or more electrodes 140 can be used to sense electrical activity or provide electrical stimulation to the free wall of the left ventricle 112. The one or more electrodes 140 are connected to the sensing amplifier 178 through conductor pair 164 and are connected to the output module 180 through conductor pair 174 wherein conductor pair 164 and conductor pair 174 allow the electrode 140 to be switched between pace mode and sense mode should intrinsic electrical activity (e.g., electrogram) at the left ventricle free wall need to be measured.

One or more electrodes 144 may be located near a distal end of the anterior lead 152 and are electrically connected to the electrode conductor pair 168/172 of lead 152. One or more accelerometers 146 may also be located near the distal end of the anterior lead 152 and are electrically connected to the accelerometer conductor pair 160 of lead 152. The one or more electrodes 144 can be used to sense electrical activity or provide electrical stimulation to the anterior wall including septum 109. The one or more electrodes 144 are connected to the sensing amplifier 178 through conductor pair 168 and are connected to the output module 180 through conductor pair 172 wherein conductor pair 168 and conductor pair 172 allow the electrode 144 to be switched between pace mode and sense mode should intrinsic electrical activity at the anterior wall need to be measured.

One or more electrodes 148 may be located near a distal end of the right ventricle lead 156 and are electrically connected to the electrode conductor pair 166/170 of lead 156. One or more accelerometers 150 may also be located near the distal end of the right ventricle lead 156 and are electrically connected to the accelerometer conductor pair 158 of lead 156. The one or more electrodes 148 can be used to sense electrical activity or provide electrical stimulation to the free wall of the right ventricle 108. The one or more electrodes 148 are connected to the sensing amplifier 178 through conductor pair 166 and are connected to the output module 180 through conductor pair 170 wherein conductor pair 166 and conductor pair 170 allow the electrode 148 to be switched between pace mode and sense mode should intrinsic electrical activity at the right ventricle free wall need to be measured.

Each lead has an inner lumen, and the accelerometers may be positioned within the lumen of each lead. A suitable lead for this purpose is the EasyTrak from Guidant Corporation. Suitable miniaturized accelerometers having a diameter of approximately 1 millimeter are available from Ball Semiconductor Inc. (see U.S. Pat. No. 6,197,610) and others, and these miniaturized accelerometers may be positioned within the inner lumen of the EasyTrak lead and positioned adjacent the lead's electrode after the lead has been properly positioned on or within the heart 100. Placing the accelerometer within the lumen of the lead is especially useful for free wall locations whereby the lead is placed within the coronary sinus vein as is ordinarily done for CRT. The accelerometer(s) may be positioned in the lumen of the lead within the coronary sinus vein, if desired, thereby minimizing the invasiveness of the accelerometer implantation.

The accelerometers 142, 146, and 150 move with the corresponding ventricular wall location during contraction, as indicated by the arrows in FIG. 3. This motion of the accelerometers 142, 146, and 150 produces signals that are transferred to accelerometer amplifier 176. The amplifier 176 then directs the signals to the accelerometer data processing module 182 of processing module 198. The accelerometer data processing module 182 may provide bandpass type filtering to re-shape the waveforms so that phase and/or amplitude differences may be more accurately extracted. The accelerometer data processing module 182 provides a detected difference in accelerometer signals measured at different ventricular wall locations to an accelerometer based optimization module 188. The logical operations of the accelerometer data processing module 182 are discussed in more detail below with reference to FIG. 4.

The accelerometer based optimization module 188 then determines whether the stimulation parameters to be applied in the next cardiac cycle should be altered to provide optimal synchronization. The logical operations of the accelerometer based optimization module 188 are discussed in more detail below with reference to FIG. 6. After determining whether to alter the stimulation parameters, the accelerometer based optimization module 188 passes the result to CRT configuration module 194. CRT configuration module 194 produces the desired CRT parameter values to be maintained by parameter module 196, such as the relative pulse timing, pulse width, pulse amplitude, and pulse location for the ventricles.

The CRT configuration module 194 may receive CRT parameter instructions from a therapy module 192, such as the energy level of pulses to be applied to the heart 100 to properly control the pulse rate and/or rhythm of the heart 100 for patients with additional arrhythmias. The therapy module 192 may compute additional parameter settings for treating arrhythmias that are not directly related to the CRT pulses, such as pacing parameters for the atrial electrode 138, which are maintained by the parameter module 196. Therapy module 192 determines the arrhythmia therapy parameter instructions in response to arrhythmia detection module 190 detecting arrhythmia conditions of the heart 100. The arrhythmia is detected by analyzing electrogram data 1 provided by an electrogram data processing module 186 that receives the intrinsic electrical activity signals through sensing electrode amplifier 178 when the electrodes are in sense mode, and may provide bandpass type filtering to the signals to generate more accurate electrograms.

Parameter module 196 controls the output module 180 by instructing the output module 180 to fire a stimulation pulse to a particular electrode at a given time, with a particular pulse width and amplitude. Output module 180 applies the desired voltage pulse across the conductor pair for the corresponding electrode to attempt resynchronization of ventricular contraction and/or elimination of the additional arrhythmia. The timing of pulses from output module 180 may be determined in relation to intrinsic atrial and/or ventricular electrical activity or in relation to previously applied electrical stimulations, depending upon the particular patient's heart condition and corresponding treatment.

To facilitate the optimization for resynchronization and/or treatment of additional arrhythmias, it is useful to compare a current mechanical response or intrinsic electrical activity to previous measurements. Therefore, memory module 184 is included to allow the accelerometer data processing module 182 and/or the electrogram data processing module 186 to store information for a current cardiac cycle for use in optimization during a subsequent cardiac cycle. During the subsequent cardiac cycle, the previous mechanical response may be used as a basis for comparison by the accelerometer based optimization module 188 regardless of whether the electrodes are in paced or sense mode. Similarly, the arrhythmia detection module 190 may use the electrogram data sensed from a previous cardiac cycle as a basis for comparison for electrogram data sensed from a subsequent cardiac cycle.

Figure 4:
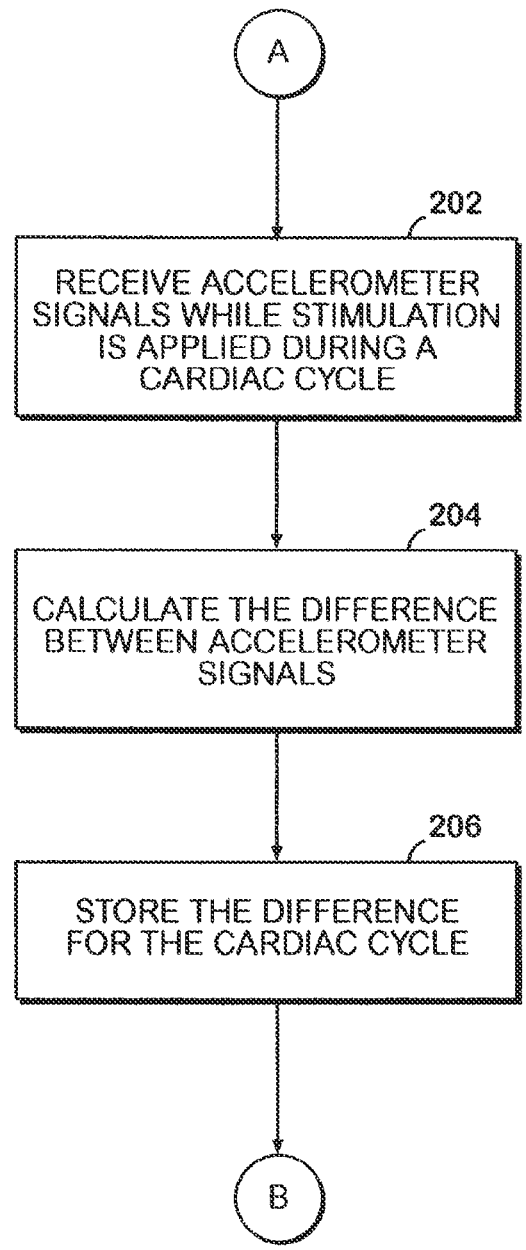
FIG. 4 is a flowchart depicting exemplary logical operations for detecting a difference between contractions at different ventricular wall locations.

FIG. 4 shows the logical operations of the accelerometer data processing module 182. The logical operations of FIG. 4 indicate that the accelerometer data processing module 182 is functioning while the electrodes are in pace mode. However, one of ordinary skill in the art will recognize that the data processing module 182 can process signals created by motion of the accelerometers for cardiac cycles where the electrodes are in sense mode, such as when the asynchronous natural ventricular contraction is to be measured. The particular accelerometers to monitor may be initially programmed into the accelerometer data processing module 182 by a physician when the blockage condition of the patient is already known. Alternatively, the device 199 may be configured to determine the condition of the patient by monitoring all accelerometers to detect a lack of synchronization of one or more cardiac walls and then applying the logical operations of FIGS. 4 and 6 for those cardiac walls to improve and maintain synchronization.

For a particular cardiac cycle, the logical operations begin at receive operation 202 where signals are received in response to motion of two or more accelerometers positioned at different ventricular wall locations. For example, if the patient has a left bundle branch block, then receive operation 202 might accept signals from at least the left ventricle free wall accelerometer 142 and the anterior wall accelerometer 146 so that both walls responsible for left ventricular contraction may be monitored. It may also be desirable to monitor the right ventricular free wall with accelerometer 150, such as when a right bundle branch block exists or when attempting to synchronize contraction of both the left and right ventricular free walls.

After receiving the accelerometer signals, flow moves to calculate operation 204 where the accelerometer data processing module 182 compares the at least two accelerometer signals to detect a difference and thereby observe asynchronous contraction. The processing module 198 may employ one or more methods of detecting a difference between the accelerometer signals. For example, the difference that is detected may be a phase difference indicating a difference in the timing of the contractions at the two ventricular wall locations. The difference may be an amplitude difference indicating a difference in the amount of contraction at the two ventricular wall locations. Such signal processing operations are well known to those skilled in the art.

Figure 5:
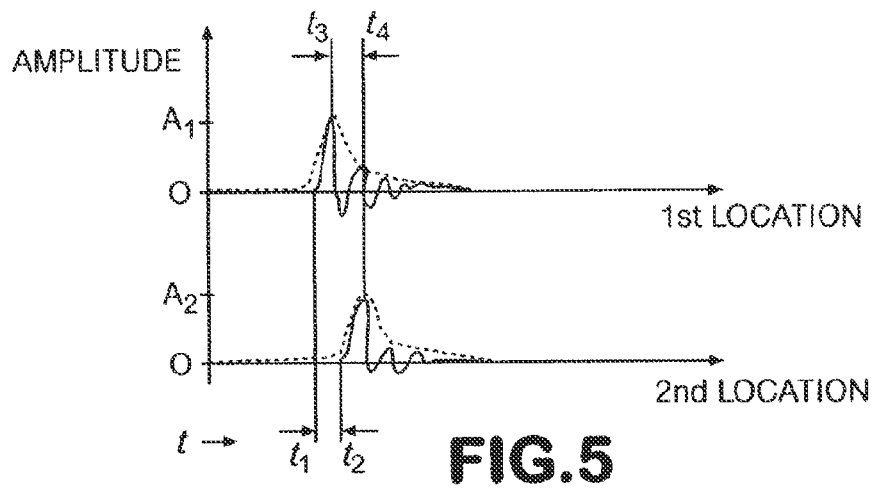
FIG. 5 is graph of a possible mechanical response of two ventricular wall locations with respect to time showing a difference in phase and amplitude as detected by the CRT device.

FIG. 5 shows a possible example of two accelerometer signals and the detection of differences between them thereby indicating some form of asynchronous contraction. The accelerometer signal from a first ventricular wall location indicates that contraction begins at $t_1$ and that the peak of contraction is at $t_3$. The accelerometer signal from a second ventricular wall location indicates that contraction begins at $t_2$ and that the peak of contraction is at $t_4$. The interval from $t_1$ to $t_2$ indicates a phase difference in relation to the beginning of contraction. Similarly, the interval from $t_3$ to $t_4$ indicates a phase difference in relation to the peak of contraction.

Comparing the interval from $t_1$ to $t_3$ to the interval from $t_2$ to $t_4$ will indicate a difference in the rate of contraction from baseline to peak for each wall location. Furthermore, the peak amplitude $A_1$ for the contraction at the first ventricular wall location can be compared to the peak amplitude $A_2$ for the contraction at the second ventricular wall location to indicate a difference in contractility of the two wall locations. One skilled in the art will recognize that several other characteristics of the two accelerometer signals can be compared to detect a form of asynchronous contraction, such as detecting a phase or amplitude difference at multiple locations. For example, the difference may be computed with reference to one or more locations along an envelope (dotted line of FIG. 4) of the accelerometer signals. As discussed, one or more of the techniques may be employed alone or in conjunction by the processing module 198 to detect asynchronous ventricular contractions.

Again with reference to FIG. 4, after the accelerometer data processing module 182 has calculated the difference between the accelerometer signals, such as shown in FIG. 5, flow transitions to store operation 206. At store operation 206, the difference value(s) detected between the two or more signals may be stored in memory module 184 to be used as a basis for comparison in subsequent cardiac cycles. For example, the difference(s) between the left ventricular free wall and anterior wall may be stored, the difference(s) between the left ventricular free wall and the right ventricular free wall may be stored, and/or the difference(s) between the right ventricular free wall and the anterior wall may be stored. After storing the difference(s) for the current cardiac cycle, operational flow transitions to the logical operations shown in FIG. 6 that are performed by the accelerometer based optimization module 188.

Figure 6:
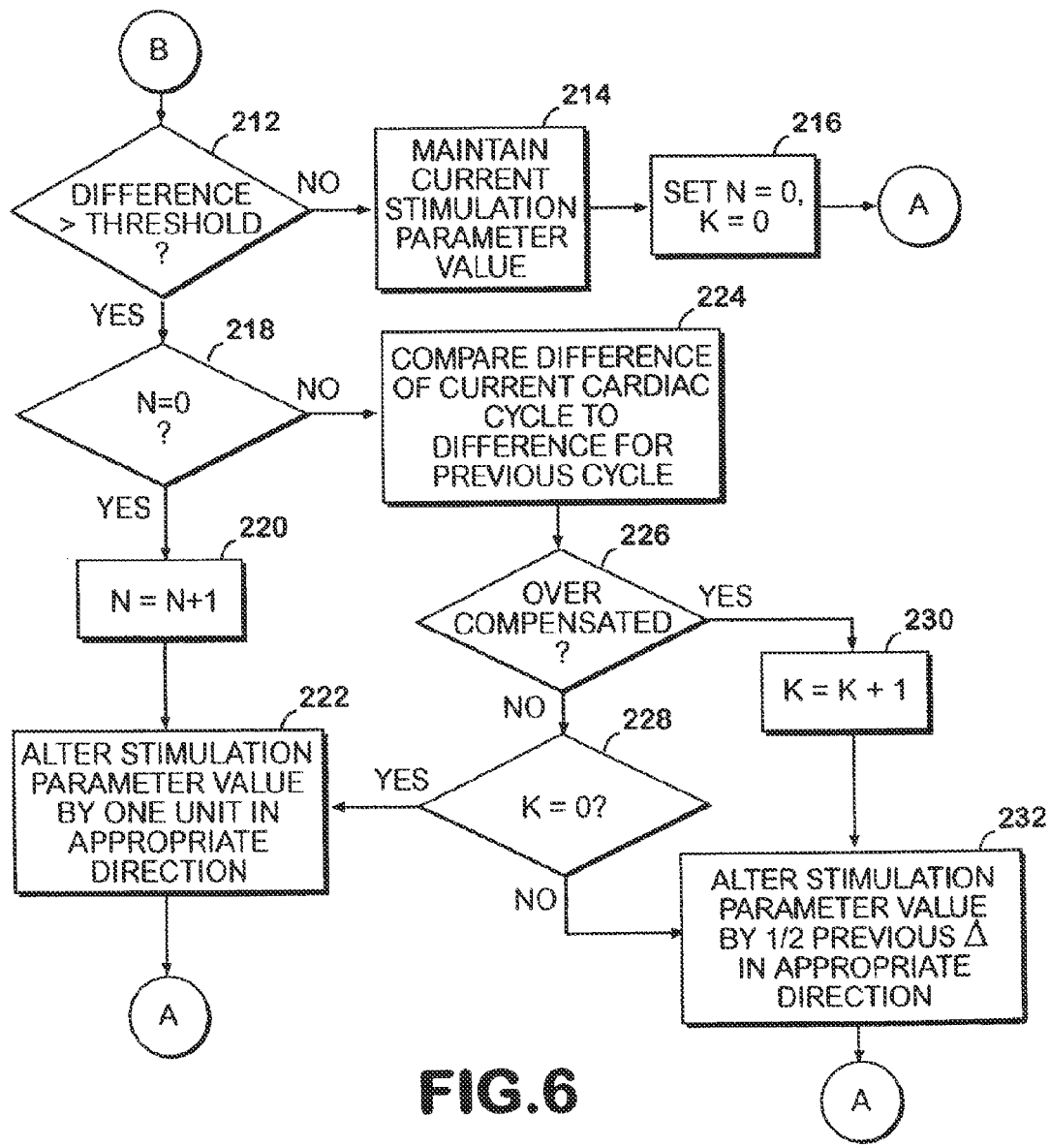
FIG. 6 is a flowchart depicting exemplary logical operations for optimizing the stimulation provided to a ventricular wall location.

The logical operations of FIG. 6 begin at query operation 212 where the optimization module 188 compares the absolute value of the difference (i.e., phase, amplitude, or other value) between the two accelerometer signals to a tolerance threshold. For example, a phase difference of +/−5 degrees or less in relation to the beginning of contraction (e.g., as measured from $t_1$ to $t_2$ of FIG. 5) may be acceptable. If this particular characteristic is being used as the determining factor of contractile synchronization, then query operation 212 compares the absolute value of the detected phase difference to the 5 degrees threshold value. If the absolute value of the detected phase difference is less than the 5 degrees threshold, then flow moves to parameter operation 214 whereby the optimization module 188 instructs the CRT configuration module 194 to maintain the current stimulation parameter values being applied by parameter module 196 to output module 180.

Flow continues to flag operation 216, where an iteration flag N and an open-loop flag K are set equal to zero. The iteration flag N is used to track whether the previous cardiac cycle was within or outside of the threshold for detecting synchronous contraction. In the embodiment shown, knowing whether the previous cardiac cycle was within or outside of the threshold is useful in determining whether to compare a difference outside of the threshold for a current cardiac cycle to a previously stored difference. If the previously stored difference was within the threshold, then it will not be used as a basis for comparison when tweaking the stimulation parameters as discussed below because the current difference outside of the threshold will be, by definition, degraded relative to the previous difference that was within the threshold. Application of the iteration flag N is discussed in more detail below.

The open-loop flag K is used to track whether the previous cardiac cycle resulted in the first overcompensation condition whereby the detected difference has reversed polarity. In the embodiment shown, an approximation of open-loop control is utilized until overcompensation results to reduce the number of cardiac cycles required to eliminate the difference between the two accelerometer signals. For example, if a phase difference is initially −25 degrees but becomes +15 degrees in the following cardiac cycle due to a maximum alteration of a stimulation parameter, then an overcompensation has resulted as indicated by the polarity change in the phase difference and K will be incremented to reflect this occurrence. Application of the open-loop flag K is discussed in more detail below as well.

After setting the flags to zero, operational flow returns to the logical operations of FIG. 4 performed by data processing module 182 for the next cardiac cycle and then back to query operation 212. If query operation 212 of FIG. 6 detects that the detected difference for a current cardiac cycle is outside of the threshold, then flow transitions to query operation 218. Query operation 218 detects whether the flag variable N is equal to zero. If so, then this indicates that the previous cardiac cycle produced a difference that was within the threshold, and as discussed above, is not useful as a basis for comparison when tweaking the parameter values. Therefore, flow transitions to counter operation 220 where the iteration flag N is incremented from zero to one.

Then, at parameter operation 222, the optimization module 188 instructs the CRT configuration module 194 to alter one or more stimulation parameter values one full unit in the direction necessary to reduce the difference. For example, if the phase difference is +25 degrees because the left ventricle free wall is contracting too early relative to the anterior wall, then the delay between atrial activity and the delivery of the left ventricle free wall stimulation should be lengthened to delay the left ventricle free wall contraction and reduce the phase difference. The one full unit is an arbitrary amount, but one skilled in the art will appreciate that the value of one unit may be chosen so as to bring about a noticeable change in the signal characteristic being used to detect the difference. Additionally, the unit of incrementation may be variable depending upon the degree of separation between the measured difference and the threshold.

After incrementing the stimulation parameter, flow returns to the logical operations of the data processing module 182 for the next cardiac cycle where the new stimulation parameter value will be implemented by output module 180. After the new difference is determined and stored, control returns to query operation 212. If the newly detected difference is still beyond the threshold, then flow transitions again to query operation 218 which will then detect that iteration flag N is greater than zero since it was incremented on the last iteration. Control then transitions to compare operation 224.

Compare operation 224 detects the change resulting from application of the altered stimulation parameter. This change is detected by comparing the difference in the two accelerometer signals for the current cardiac cycle to the difference in the two accelerometer signals for the previous cardiac cycle. For example, the previous cardiac cycle may have produced a phase difference of −25 degrees and the current cardiac cycle produced a phase difference of −10 degrees which indicates a positive change of 15 degrees. Thus, the alteration to the stimulation parameter was in the proper direction but was too small to adequately synchronize the contraction of the ventricular wall locations. Query operation 226 then uses this comparison to determine whether the last change in the stimulation parameter value created an overcompensation. In this example, no overcompensation occurred because the polarity of the phase difference did not change.

If query operation 226 detects that no overcompensation has occurred, then flow transitions to query operation 228 which tests whether the open-loop flag K is equal to zero. For each iteration when open-loop flag K is equal to zero, open-loop control is approximated by query operation 228 directing flow back to parameter operation 222 where the stimulation parameter is again altered by one full unit. However, once query operation 226 detects an overcompensation from compare operation 224 finding a change in polarity of the difference, flow is directed to counter operation 230 where the open-loop flag K is incremented. Then, parameter operation 232 alters the stimulation parameter value for application in the next cardiac cycle. If query operation 226 detects that no overcompensation has occurred, but query operation 228 detects that open-loop flag K does not equal zero, then flow will proceed to parameter operation 232.

Parameter operation 232 adds or subtracts based upon the direction of change needed to bring the difference to its ideal value, generally zero. For example, if the phase difference was −30 degrees but due to overcompensation is now +25 degrees thereby indicating that the left ventricle free wall has contracted too early, then parameter operation 232 may add one-half of the last change ($\Delta$) to the delay for the pulse. If the previous $\Delta$ resulting in overcompensation was a subtraction of Y milliseconds which resulted in a delay of X milliseconds, then parameter operation 232 will add Y/2 milliseconds back to the delay of X milliseconds to delay application of the left ventricle free wall pulse.

Parameter operation 232 functions in the same manner when overcompensation has not resulted from the previous $\Delta$ but when open-loop flag K does not equal zero due to overcompensation having occurred in some previous cardiac cycle. For example, if the phase difference was +30 degrees after overcompensation and is now +25 degrees due to a $\Delta$ being an addition of Z milliseconds, then parameter operation 232 may add one half of the previous $\Delta$, or Z/2, to the current parameter value. Through parameter operation 232 adding or subtracting the previous $\Delta$ divided by two, depending upon the direction needed to approach a difference of zero, the difference between the two accelerometer signals is reduced to zero (or within the threshold amount if other than zero) in a closed-loop fashion. Thus, this manner of altering the stimulation parameter value operates without regard to whether the mechanical response of the heart 100 is linear with respect to a change of the stimulation parameter value.

One of ordinary skill in the art will recognize that other manners of reducing the detected difference to zero are possible. For one alternative, rather than altering the parameter value in an open-loop fashion until reaching overcompensation and then applying the $\Delta$/2 adjustment routine, the change resulting from a parameter value alteration can be compared to the difference from the ideal. For example, if the phase difference is initially +25 degrees and one full unit of change produces a phase difference of +10 degrees (i.e., a change of −15 degrees), wherein zero is ideal, then altering the parameter value by (10-0)/(25-10), or two-thirds of a unit, will likely bring the difference closer to the ideal within one iteration than will simply altering the parameter by ½Δ (i.e., ½ unit in this example). This example, however, assumes a relatively linear relationship between mechanical response and parameter value alteration.

Another alternative approach is to establish a numerical relationship between the accelerometer output signal (i.e., phase difference) and the stimulation signal (i.e., parameter change). The relationship may or may not be linear between a parameter change and a change in phase difference. By repetitively applying a change and measuring the phase difference, a record may be constructed from which the numerical relationship may be found. The numerical relationship may then be applied in a closed-loop, negative feedback control system to optimize and maintain the synchronization of the wall contractions.

The logical operations of FIGS. 4 and 6 may be applied in parallel for two pairs of signals having one signal in common. For example, if the right ventricle free wall, anterior wall, and left ventricle free wall must be brought into synchronization, one branch of operations may be acting upon the right ventricle free wall signal in relation to the reference anterior wall signal while the other branch of operations are acting upon the left ventricle free wall signal in relation to the same reference anterior wall signal. One skilled in the art will recognize that several permutations of this parallel processing scheme are possible for providing synchronization to multiple ventricular wall locations. Furthermore, the logical operations of FIGS. 4 and 6 may operate on left ventricle free wall motion versus right ventricle free wall motion, anterior wall versus free wall motion, or motion of one location on a ventricular wall versus motion of another location on the same ventricular wall (i.e., synchronizing two locations on the left ventricle free wall).

It should to be understood that the logical operations for detecting the difference between the accelerometer signals and for determining the appropriate stimulation parameter value may be performed by a device other than the implantable or external CRT device, such as by an external device programmer communicating via telemetry. Furthermore, the logical operations may be implemented (1) as a sequence of computer implemented steps running on a computer system, and/or (2) as interconnected machine modules such as processing module 198 running within the computing system.

This implementation is a matter of choice dependent on the performance requirements of the CRT device 199 or device programmer implementing the invention. Accordingly, the logical operations making up the embodiments of the invention described herein are referred to as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

While the invention has been particularly shown and described with reference to preferred embodiments thereof, it will be understood by those skilled in the art that various other changes in the form and details may be made therein without departing from the spirit and scope of the invention.

What is claimed is:

1. A method comprising:
    sensing motion of a heart contraction at a first heart to produce a first signal;
    sensing motion of the heart contraction at a second heart wall location to produce a second signal;
    comparing the first signal to the second signal to detect a difference in synchronization of the first heart wall location with respect to the second heart wall location; and
    iteratively adjusting a control parameter of a stimulation pulse to reduce the difference in synchronization.

2. The method of claim 1, wherein comparing the first signal to the second signal comprises comparing at least one of an amplitude, a time of peak contraction, or a time of an onset of contraction indicated by the first signal with respect to a corresponding measurement indicated by the second signal.

3. The method of claim 1, wherein iteratively adjusting the control parameter comprises:
    determining a magnitude of the difference in synchronization of the first heart wall location with respect to the second heart wall location; and
    adjusting the control parameter based on the magnitude determined.

4. The method of claim 3, wherein the determining the magnitude and adjusting the control parameter based on the magnitude are performed until the difference in synchronization is within an acceptable threshold of dyssynchrony, 5. The method of claim 1, wherein iteratively adjusting the control parameter comprises using a root finding function.

6. The method of claim 5, wherein the root finding function is a bisection method.

7. The method of claim 1, wherein the difference in synchronization comprises a phase difference, and wherein iteratively adjusting the control parameter comprises:
    identifying a stimulation parameter by referencing a pre-established relationship between the phase difference and the stimulation parameter; and
    adjusting the control parameter using the stimulation parameter.

8. A machine-readable storage medium comprising instructions, which when executed by a machine, cause the machine to:
    sense motion of a heart contraction at a first heart wall location to produce a first signal;
    sense motion of the heart contraction at a second heart wall location to produce a second signal;
    compare the first signal to the second signal to detect a difference in synchronization of the first heart wall location with respect to the second heart wall location; and
    iteratively adjust a control parameter of a stimulation pulse to reduce the difference in synchronization.

9. The machine-readable storage medium of claim 8, wherein the instructions to compare the first signal to the second signal comprise instructions, which when executed on the machine, cause the machine to compare at least one of an amplitude, a time of peak contraction, or a time of an onset of contraction indicated by the first signal with respect to a corresponding measurement indicated by the second signal.

10. The machine-readable storage medium of claim 8, wherein the instructions to iteratively adjust the control parameter comprise instructions, which when executed on the machine, cause the machine to:
    determine a magnitude of the difference in synchronization of the first heart wall location with respect to the second heart wall location; and adjust the control parameter based on the magnitude determined.

11. The machine-readable storage medium of claim 10, wherein the instructions to determine the magnitude and adjust the control parameter based on the magnitude are performed until the difference in synchronization is within an acceptable threshold of dyssynchrony.

12. The machine-readable storage medium of claim 8, wherein the instructions to iteratively adjust the control parameter comprise instructions, which when executed on the machine, cause the machine to use a root finding function.

13. The machine-readable storage medium of claim 12, wherein the root finding function is a bisection method.

14. The machine-readable storage medium of claim 8, wherein the difference in synchronization comprises a phase difference, and wherein the instructions to iteratively adjust the control parameter comprise instructions, which when executed on the machine, cause the machine to:
- identify a stimulation parameter by referencing a pre-established relationship between the phase difference and the stimulation parameter; and
- adjust the control parameter using the stimulation parameter.

15. An apparatus comprising:
- a first motion sensor located at a first heart wall location and configured to produce a first signal;
- a second motion sensor located at a second heart wall location and configured to produce a second signal;
- a processor, coupled to the first and second motion sensors, the processor configured to:
  - compare the first signal to the second signal to detect a difference in synchronization of the first heart wall location with respect to the second heart watt location; and
  - iteratively adjust a control parameter of a stimulation pulse to reduce the difference in synchronization.

16. The apparatus of claim 15, wherein the processor is configured to:
- determine a magnitude of the difference in synchronization of the first heart wall location with respect to the second heart wall location; and
- adjust the control parameter based on the magnitude determined.

17. The apparatus of claim 16, wherein the processor is configured to determine the magnitude and adjust the control parameter based on the magnitude until the difference in synchronization is within an acceptable threshold of dyssynchrony.

18. The apparatus of claim 15, wherein the processor is configured to use a root finding function to iteratively adjust the control parameter.

19. The apparatus of claim 18, wherein the root finding function is a bisection method.

20. The apparatus of claim 15, wherein the difference in synchronization comprises a phase difference, and wherein the processor is configured to iteratively adjust the control parameter by:
- identifying a stimulation parameter by referencing a pre-established relationship between the phase difference and the stimulation parameter; and
- adjusting the control parameter using the stimulation parameter.

* * * * *